(12) United States Patent
Nelson

(10) Patent No.: US 7,243,653 B2
(45) Date of Patent: Jul. 17, 2007

(54) INTUBATION DEVICE

(75) Inventor: Lindsey A. Nelson, Cincinnati, OH (US)

(73) Assignee: Radlyn LLC, Cincinnati, OH (US)

( * ) Notice: Subject to any disclaimer, the term of this patent is extended or adjusted under 35 U.S.C. 154(b) by 0 days.

(21) Appl. No.: 10/455,929

(22) Filed: Jun. 6, 2003

(65) Prior Publication Data

US 2006/0081253 A1      Apr. 20, 2006

(51) Int. Cl.
*A61M 16/00*      (2006.01)

(52) U.S. Cl. ............................. 128/207.14; 128/200.26

(58) Field of Classification Search ........... 128/200.26, 128/207.14, 207.15, 207.16; 604/164.11, 604/164.12, 164.13, 170.01, 170.02, 170.03, 604/171
See application file for complete search history.

(56) References Cited

U.S. PATENT DOCUMENTS

| | | | | |
|---|---|---|---|---|
| 3,957,055 A | | 5/1976 | Linder et al. ............... 128/351 |
| 3,996,939 A | * | 12/1976 | Sheridan et al. ....... 128/207.14 |
| 4,150,676 A | * | 4/1979 | Jackson ................. 128/207.18 |
| 4,244,362 A | * | 1/1981 | Anderson .............. 128/200.26 |
| 4,329,983 A | | 5/1982 | Fletcher ................. 128/207.14 |
| 4,529,400 A | | 7/1985 | Scholten ...................... 604/95 |
| 4,593,687 A | | 6/1986 | Gray et al. ................. 128/200 |
| 4,637,388 A | * | 1/1987 | Melendy ................ 128/207.14 |
| 4,685,457 A | * | 8/1987 | Donenfeld ............. 128/207.14 |
| 4,865,586 A | * | 9/1989 | Hedberg .................... 604/93.01 |
| 4,925,445 A | * | 5/1990 | Sakamoto et al. .......... 604/528 |
| 4,949,716 A | | 8/1990 | Chenoweth ............ 128/207.14 |
| 5,058,577 A | * | 10/1991 | Six ........................ 128/200.26 |
| 5,178,158 A | * | 1/1993 | de Toledo ................... 600/585 |
| 5,235,970 A | * | 8/1993 | Augustine .............. 128/200.26 |
| 5,259,377 A | | 11/1993 | Schroeder .............. 128/207.14 |
| 5,558,082 A | * | 9/1996 | Spencer ................. 128/200.26 |
| 5,704,926 A | * | 1/1998 | Sutton ........................ 604/526 |
| 5,772,609 A | * | 6/1998 | Nguyen et al. ............. 600/585 |
| 5,819,727 A | | 10/1998 | Linder ................... 128/200.26 |
| 5,919,183 A | * | 7/1999 | Field ........................... 604/530 |
| 6,161,537 A | * | 12/2000 | Gravenstein et al. ... 128/200.26 |
| 6,340,441 B1 | * | 1/2002 | Meyer et al. .......... 264/173.12 |
| 6,463,927 B1 | | 10/2002 | Pagan ................... 128/200.26 |
| 6,539,942 B2 | | 4/2003 | Schwartz et al. ...... 128/207.14 |
| 6,550,475 B1 | | 4/2003 | Oldfield ................ 128/200.26 |
| 6,672,308 B1 | * | 1/2004 | Gaspari ................. 128/207.14 |
| 6,718,970 B2 | * | 4/2004 | Sniadach ............... 128/200.26 |
| 6,843,769 B1 | * | 1/2005 | Gandarias ................... 600/189 |
| 7,014,616 B2 | * | 3/2006 | Ferrera ....................... 600/585 |

* cited by examiner

*Primary Examiner*—Teena Mitchell
(74) *Attorney, Agent, or Firm*—Mark F. Smith; Smith Brandenburg Ltd

(57) ABSTRACT

The present invention is a device and a method of performing endotracheal intubation. In a preferred embodiment of the invention, the intubation device comprises an endotracheal tube having a forward open end, a rearward open end, and an inner bore there between. The endotracheal tube is provided with a fitting for inserting longitudinally within the rearward end and an adaptor for connecting to a respirator or other ventilating apparatus. A stylet is telescopingly positioned within the inner bore and extends outwardly from the forward open end and includes a longitudinally extending soft and flexible guide portion. The stylet is adapted to move outwardly from the forward open end of the endotracheal tube such that during insertion of the endotracheal tube into the trachea of the patient the guide portion is positioned within the trachea and operates to direct the endotracheal tube within the trachea.

12 Claims, 8 Drawing Sheets

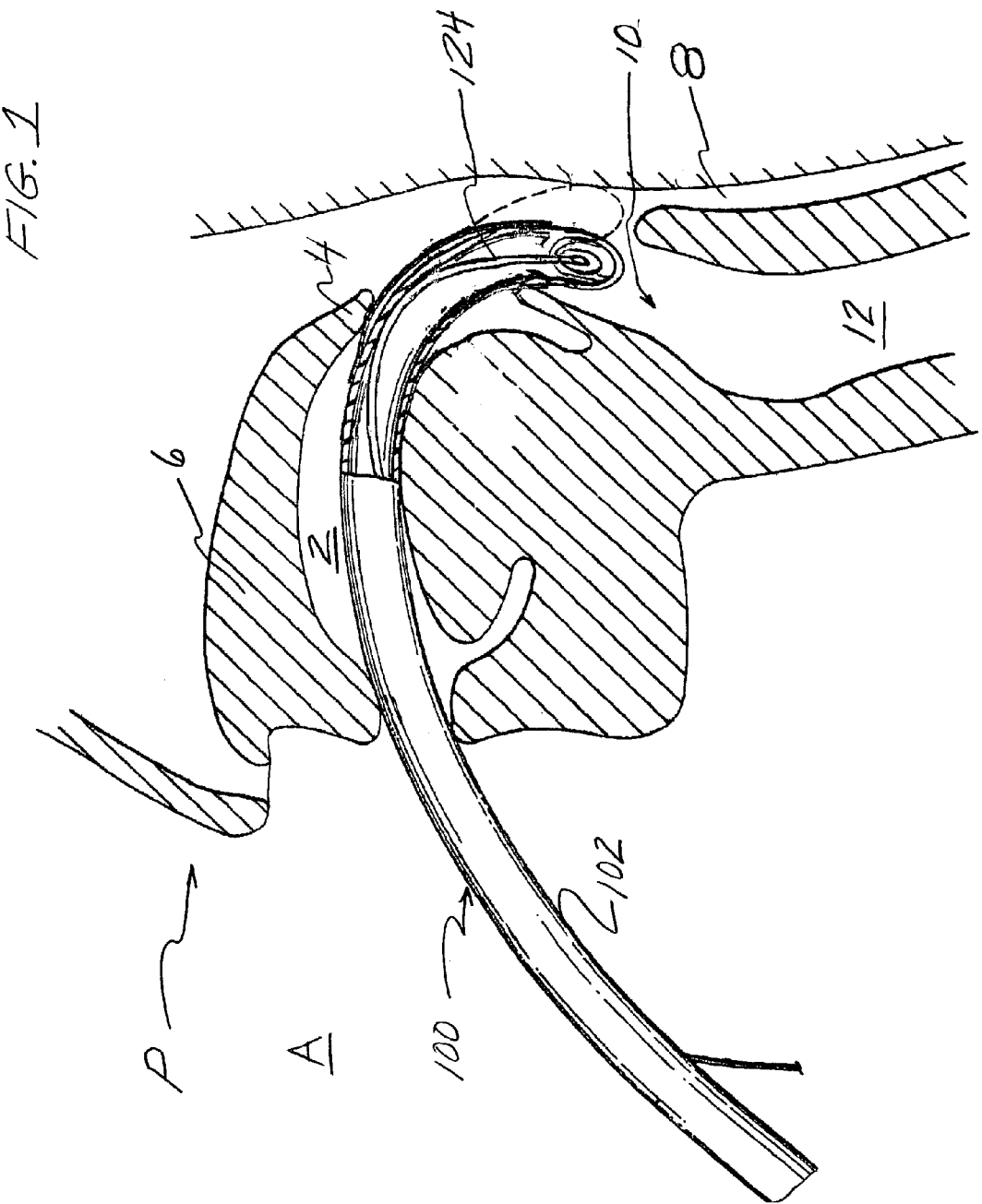

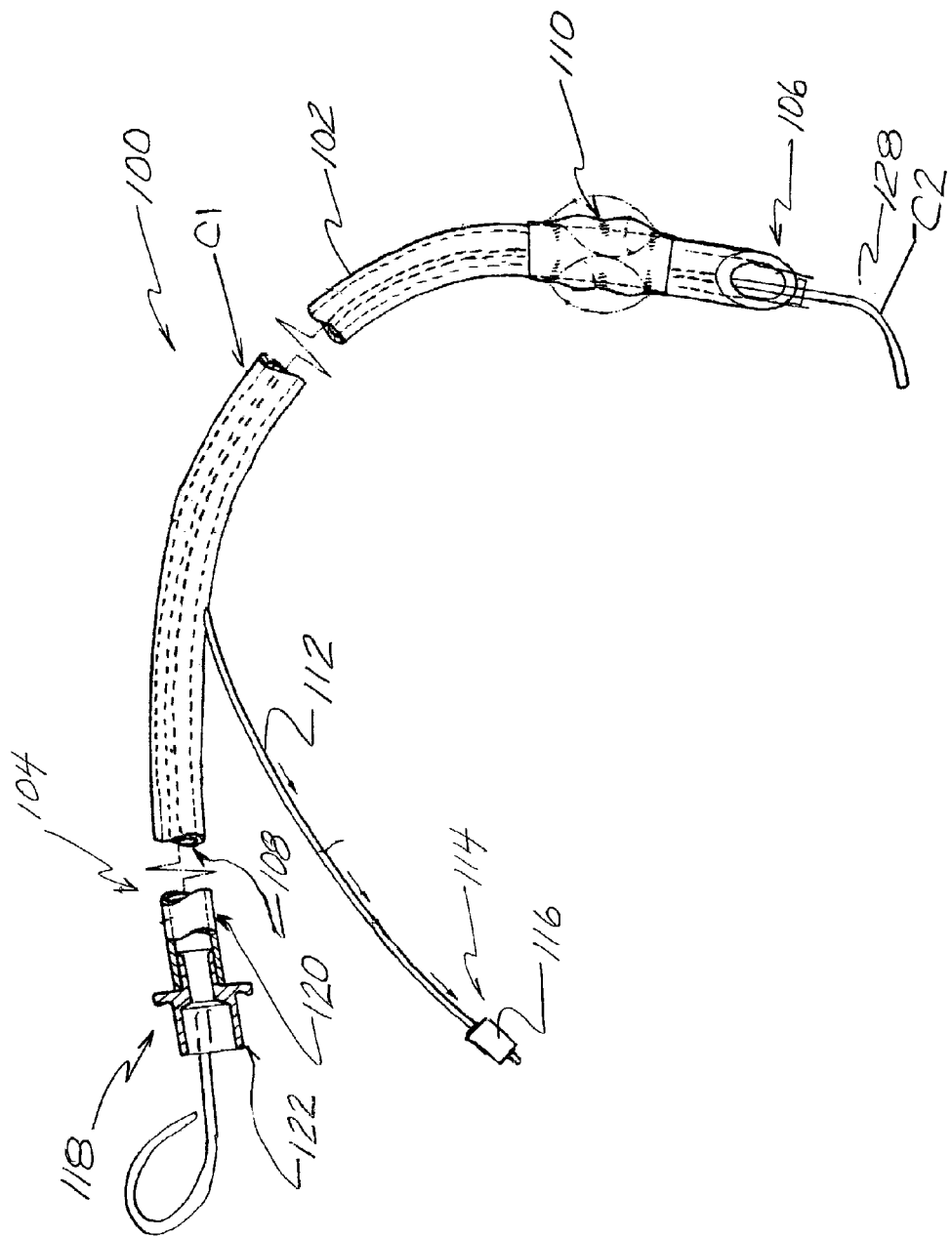

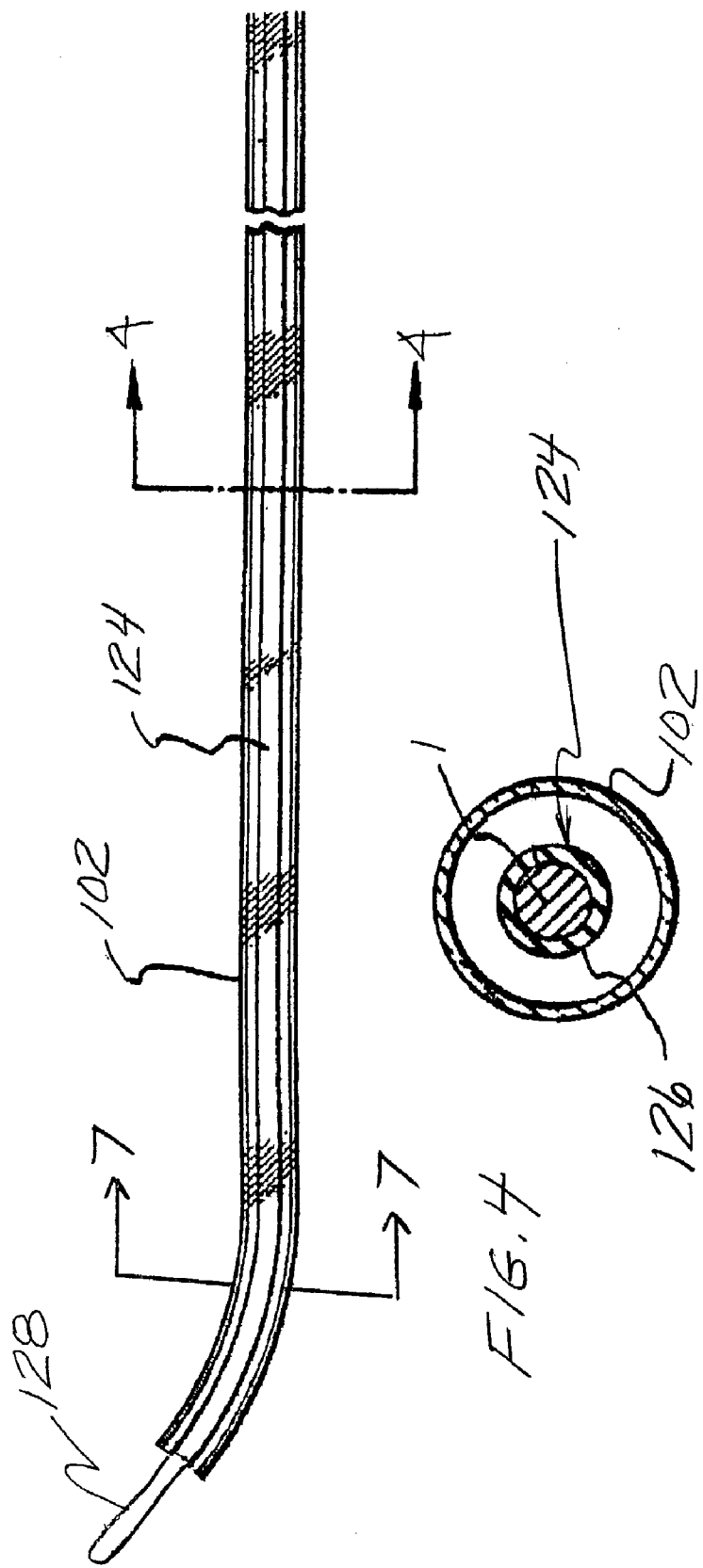

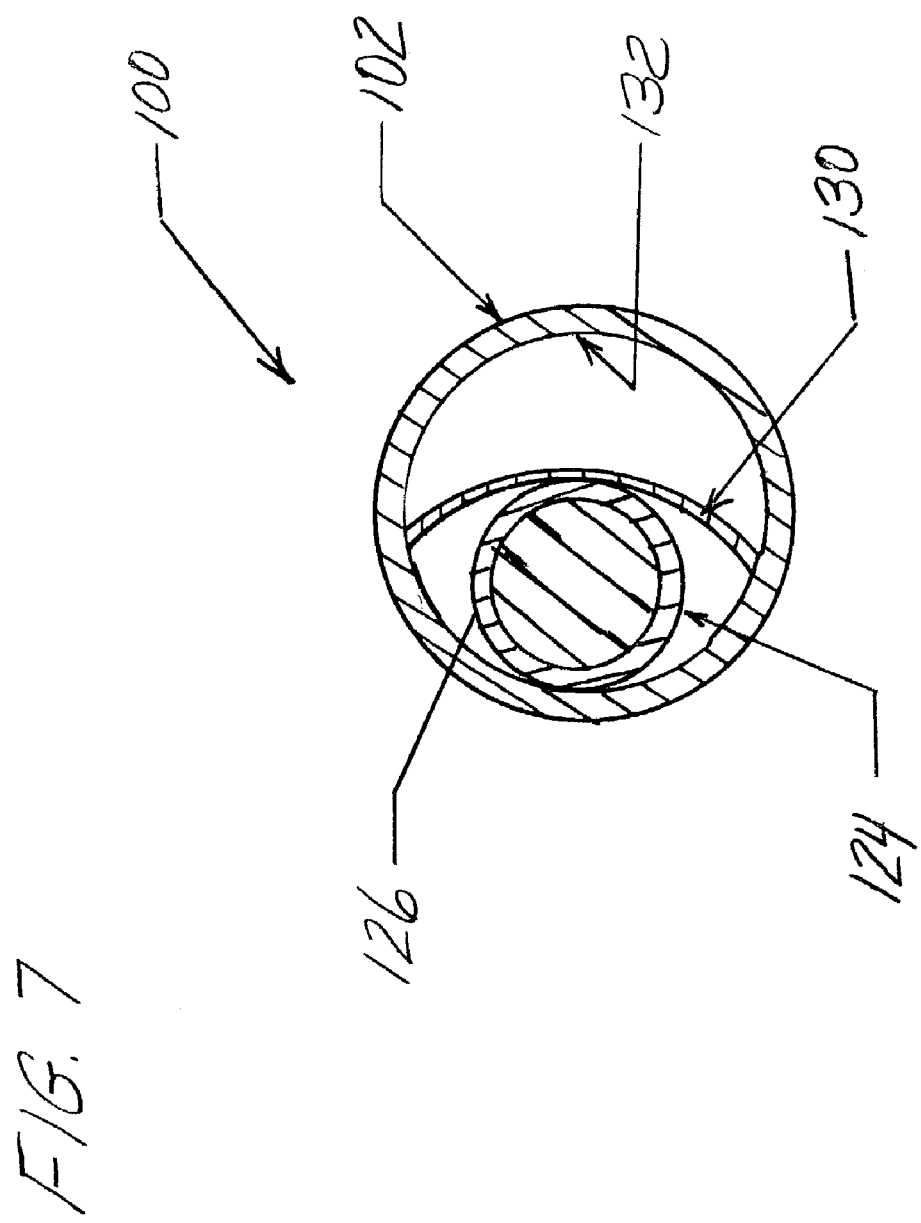

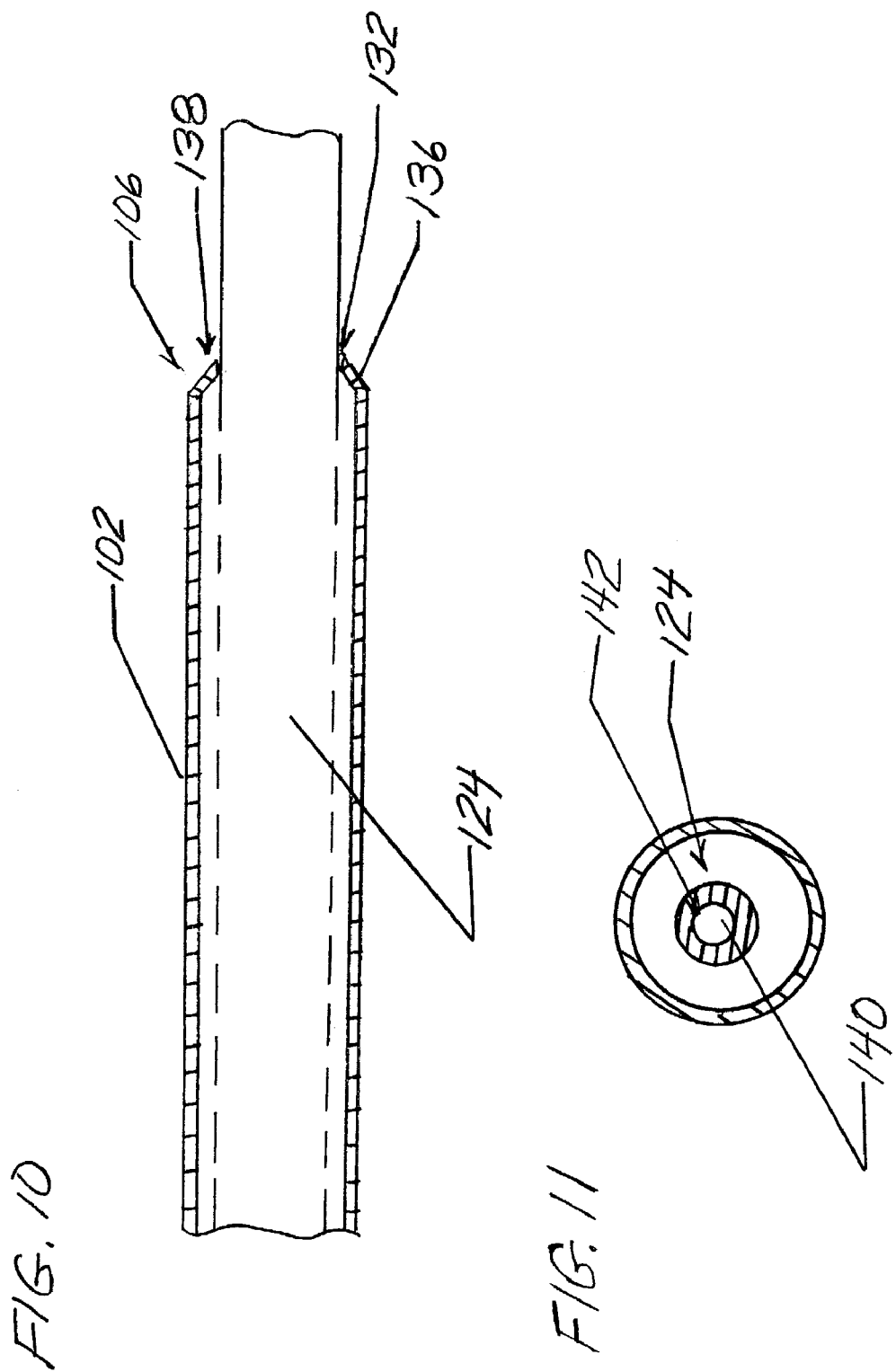

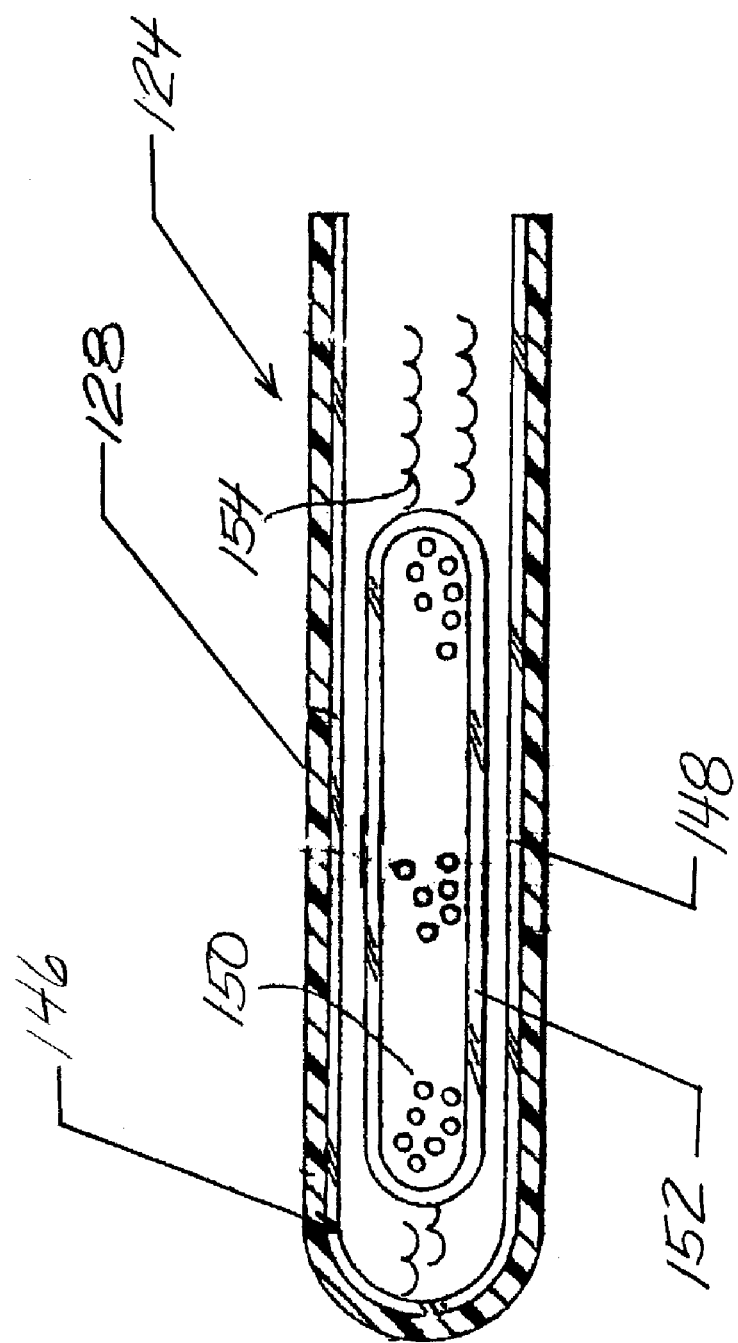

INTUBATION DEVICE

BACKGROUND OF THE INVENTION

This invention relates to an intubation tube and more particularly, to a new and improved intubation device having a stylet for use in placing an endotracheal tube into the trachea of a patient.

Intubation devices, such as oral-endotracheal tubes, are utilized in a wide variety of medical situations to provide an unobstructed conduit to a patient's trachea in which oxygen, medications and therapies can be passed. In most situations in which medical attention is needed, medical personnel will first determine the ability of the patient to maintain their airway. Often these emergent evaluations are performed by individuals having inadequate training and knowledge in airway management. The inability to secure an airway and provide a route of ventilation in someone whose airway is threatened, compromised, or obstructed can quickly result in irreversible brain damage and death.

Placement of an intubation device, such as an endotracheal tube, into the tracheobronchial tree of a patient is accessed via the nasal or oral opening. In a few select situations nasal intubation is indicated, however, the vast majority of airways are secured via the oraltracheal route. Placement of an endotracheal tube, however, is often found to be a difficult procedure, even by well-trained, experienced personnel. This difficulty can be attributed to the anatomical variations or the encountered situation in which the airway needs to be secured. Further, during the process of placing an endotracheal tube into the trachea of a patient, it is not uncommon that only minimal visualization of the laryngeal anatomy can be obtained thereby increasing the chances that esophageal intubation can occur. Thus, the ability to "blindly" place an endotracheal tube properly into the trachea of a patient is directly proportional to the medical personnel's experience and the availability of additional intubation devices available.

Endotracheal tubes are generally formed of soft, pliable plastic materials that increase in plasticity in the warm humidified air encountered when passing through the hypopharynx, thereby increasing the difficulty of placing an endotracheal tube through the glottic opening even under the most optimal visualization. Making the endotracheal tube out of a stiffer material, however, is not an acceptable alternative because it would cause excessive trauma to the nasal or throat tissue as the laryngeal and surrounding mucosa is extremely sensitive to manipulation. This can result in significant swelling and decreased visualization, which prevents or hinders oral tracheal intubation thereby placing the patient's life in great jeopardy. To overcome this problem, intubation devices often have a removable stylet made out of a somewhat malleable material that is telescopically placed within the endotracheal tube and has a sufficient amount of stiffness in order to maintain the tubes desired contour and to aid in tracheal intubation.

The stylet, which has gained the most acceptances for oral intubation, is a "pre-bend" stylet made of a rigid, malleable material such as rubber or plastic coated metal. Typically, during the intubation process, the medical personnel performing the process inserts the stylet into the endotracheal tube and folds one end of the stylet around the outboard end of the tube. The tube and the stylet are then molded to approximately conform to what is believed to be the route of passage to the laryngeal inlet. With the help of a laryngoscope, the medical personnel inserts the stylet and the endotracheal tube into the patient's mouth and hypopharynx until it reaches the patient's trachea. If needed, after visualizing the hypopharynx, the tube and stylet can be removed and the contour adjusted if necessary. Unfortunately, it is difficult for medical personnel, even after extensive training, to predetermine the proper contour that the endotracheal tube should be molded to for placement into the patient's trachea. Accordingly, it is not uncommon to fail in the first attempt to intubate the patient. In such an event, medical personnel must then remove the tube and the stylet from the patient, adjust their contour, re-ventilate the patient, and reinsert the now adjusted tube and stylet into the patient. Such removal and reinsertion of the endotracheal tube and stylet results in valuable time lost and may also result in damage to the patient's soft airway tissue thereby significantly increasing the likelihood of loss of visualization of the laryngeal anatomy and the time for oxygen delivery. Further, sterility of the endotracheal tube may be sacrificed when the user grasps the stylet to rebend the stylet into the proper contour.

In order to overcome some of the problems encountered with such intubation devices, mechanical guides have been developed to assist intubation of endotracheal tubes. It has been found that such mechanical guides are typically difficult to manipulate with one hand and do not allow for delicate control or provide the proper sensitivity necessary to intubate a patient quickly with a minimum amount of trauma to sensitive tissue. Accordingly, such mechanical guides have not met with widespread commercial success or recognition in the medical field and the malleable or "preb-end" stylet is still the predominate oral intubation aid used. Further, such guides are also typically formed from materials that are sufficiently rigid to maintain a desired contour. Accordingly, such guides have been found to cause trauma to sensitive tissue.

It is therefore desirable to have an intubation device that can be quickly and easily inserted to form an unobstructed conduit to a patient's trachea in which oxygen, medications and therapies can be passed, that reduces the likelihood of trauma to the sensitive nasal or throat tissue of the laryngeal and surrounding mucosa, that reduces the chances of compromising the sterility of the device, and which can be relatively inexpensive to manufacture.

SUMMARY OF THE INVENTION

The present invention is a method of performing endotracheal intubation and new and novel intubation device for performing the method. In a preferred embodiment of the invention, the intubation device for use in medical intubation comprises an endotracheal tube having a forward open end and a rearward open end and an inner bore there between. The endotracheal tube is provided with a fitting having a neck portion for inserting longitudinally within the rearward open end and an adaptor for connecting to a respirator or other ventilating apparatus. A stylet is slidably and telescopingly positioned within the inner bore and includes a proximal end that extends outwardly from the rearward open end and adaptor and a distal end having a longitudinally extending soft and semi-flexible guide portion. The stylet is adapted to slide or move outwardly from the forward open end of the endotracheal tube such that during insertion of the endotracheal tube the guide portion moves towards the larynx until it is positioned within the trachea. Thereafter, the endotracheal tube telescopingly slides or moves forwardly over the stylet and guide portion which operates to direct the endotracheal tube into proper position within the trachea. The stylet can then be removed by withdrawing the stylet rearwardly out through the rearward open end of the endotracheal tube and fitting. The endotracheal tube can then be attached to a respirator or other ventilating apparatus using the adaptor.

In another preferred embodiment of the invention, the endotracheal tube is provided with an inflatable bladder or balloon that when inflated prevents ventilation gas flowing through the endotracheal tube from escaping outwardly from the trachea.

In another preferred embodiment of the invention, the stylet is formed from a semi-flexible metal rod or wire.

In another preferred embodiment of the invention, the semi-flexible metal rod is formed from copper.

In another preferred embodiment of the invention, the metal rod is coated by a soft and pliable plastic, such as a polyethylene material.

In another preferred embodiment of the invention, the stylet is tapered to minimize the lip formed between the forward open end of the endotracheal tube and the stylet.

In another preferred embodiment of the invention, the forward open end of the endotracheal tube includes a cuff to minimize the lip formed between the forward end of the endotracheal tube and the stylet.

In another preferred embodiment of the invention, the endotracheal tube includes an inner sleeve adapted for receiving stylet to permit the endotracheal tube and stylet to be bent into a desired contour with greater unity.

In another preferred embodiment of the invention, the intubation device of the present application further comprises means for inducing curvature to the endotracheal tube and stylet.

In another preferred embodiment of the invention, the stylet includes a longitudinally extending hollow core having a proximal open end and a distal open end adapted to connect to a standard oxygen supply.

In another preferred embodiment of the invention, the stylet includes a chemiluminesent light effective for aiding in the intubation of the patient.

In a preferred embodiment of the invention the method of performing endotracheal intubation of a patient, the method comprises the steps of first inserting an endotracheal tube and a stylet of an intubation device through the mouth of a patient and down the throat towards the larynx. The stylet is then slid or moved outwardly from the endotracheal tube such that the soft and semi-flexible guide portion of the stylet enters the trachea. The stylet then operates to direct the endotracheal tube into proper position within the trachea. The stylet is then removed out through the rearward open end of the endotracheal tube and the endotracheal tube is then attached to a respirator or other ventilating apparatus.

In another preferred embodiment of the invention the curvature of the stylet is adjusted to a desired contour for insertion into the trachea of the patient.

In another preferred embodiment of the invention, the stylet having a chemiluminesent light is bent to activate the chemiluminesent light.

In another preferred embodiment of the invention, an inflatable bladder or balloon is inflated to prevent ventilation gas from flowing through the endotracheal tube from escaping outwardly from the trachea.

Other advantages of the invention will be apparent from the following description, the accompanying drawings and the appended claims.

BRIEF DESCRIPTION OF THE DRAWINGS

To provide a more complete understanding of the present invention and further features and advantages thereof, reference is now made to the following description taken in conjunction with the accompanying drawings, in which:

FIG. 1 is a partial view showing the oral passageway of a patient for the exchange of gasses between the lungs and the outside atmosphere and showing the intubation device of the present invention partially inserted;

FIG. 2 is a side view of the intubation device of FIG. 1;

FIG. 3 is a side view of the intubation device of FIG. 1 showing the stylet in its unsheathed position within the endotracheal tube;

FIG. 4 is a rearward sectional view of the intubation device of FIG. 1 with the stylet positioned in its sheathed position within the endotracheal tube and showing the stylet and the soft and pliable plastic sleeve;

FIG. 7 is a rearward sectional view of another preferred embodiment of the invention showing the inner wall of the endotracheal tube having an inner sleeve adapted for receiving the stylet;

FIG. 10 is a partial view of another preferred embodiment of the invention showing the forward open end of the endotracheal tube having a cuff for minimizing the lip formed between the forward open end of the endotracheal tube and the stylet;

FIG. 11 is a rearward sectional view of another preferred embodiment of the invention showing the stylet having a longitudinally extending hollow core; and FIG. 12 is a partial side view of the guide portion of the stylet showing the chemiluminesent light.

DETAILED DESCRIPTION OF THE INVENTION

Figure 6:
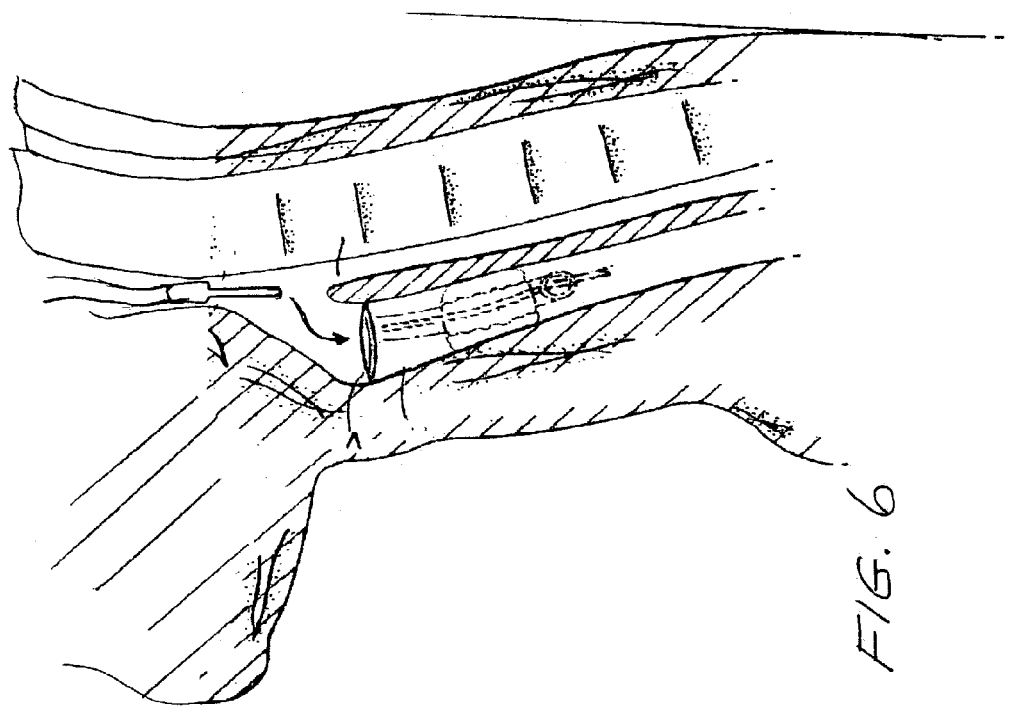
FIG. 6 is a partial view showing oral intubation of a patient utilizing the intubation device of the present invention with the endotracheal tube within the tracheal and the inflatable bladder inflated to prevent ventilation gas from flowing through the endotracheal tube from escaping outwardly from the trachea.

The present invention relates to a method of performing endotracheal intubation and a new and novel intubation device for performing the method. In describing the preferred embodiments of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose.

For purposes of the description of the present invention, the terms "forward" and "forwardly" are intended to refer to the direction towards the patient receiving the intubation device, whereas the terms "rear" and "rearwardly" are intended to refer to the direction away from the patient receiving the intubation device.

Referring to FIG. 1, a partial cross-section of a patient P is shown illustrating the mouth 2, the epiglottis 4, the nasopharynx 6, the esophagus 8 that operates to transfer food to the stomach (not shown), the larynx 10, and the trachea 12 that operates to provide a passageway for the exchange of gasses between the lungs (not shown), the alveoli (not shown), and the outside atmosphere A.

Referring to FIG. 2, the intubation device 100 of the present application is shown comprising an elongated endotracheal tube 102 having a rearward open end 104 and a forward open end 106 having a longitudinal bore 108 therebetween. The endotracheal tube 102 is formed of a pliable semi-rigid, soft plastic material such as, but not limited to, a polyethylene, a polypropylene, or like material. The lower forward end of the endotracheal tube 102 includes one or more inflatable bladders or balloons 110 which is attached to an air device through an air line 112 such that when inflated the bladder 110 operates to prevent ventilation gas flowing through the endotracheal tube 102 from escaping outwardly from the trachea 12 of the patient P. A portion of the air line 112 is preferably positioned within the wall of the endotracheal tube 102 and provides flow communication between the bladder 110 and an external air source (not shown). The rearward end 114 of the air line 112 is provided with a flow valve 116 to permit a syringe (not shown) or other inflation device to be placed in flow communication with the air line 112 for injecting a predetermined amount of air into the bladder 110.

The rearward open end 104 of the endotracheal tube 102 is provided with a fitting 118 having a neck portion 120 for inserting longitudinally within the rearward open end 104 and an adaptor 122 for connecting to a respirator or other ventilating apparatus or oxygen supply, anesthesia supply, or some other medical gas supply.

Referring to FIGS. 2, 3 and 4, telescopically positioned within the endotracheal tube 102 is an elongated stylet 124 which is formed from a semi-flexible material that can be bent relatively easily into a desirable contour, such as AWG 6-14 cooper wire of a circular cross section or some other suitable material that can be bent into a desired contour and rigid enough to support and help maintain the endotracheal tube 102 in a desired contour. The stylet 124 includes a soft and pliable plastic sleeve 126 formed from a plastic, such as a polyethylene, polypropylene, polyvinylchloride, or the like, or a rubber composition. The sleeve 126 covers the entire length of the stylet 124 and extends longitudinally outwardly from the forward end of the stylet 124 to form a soft, flexible and malleable guide portion 128. The rearward end of the stylet 124 extends longitudinally outwardly through the endotracheal tube 102 and fitting 118 such that medical personnel can easily grasp the end of the stylet 124 during the intubation procedure. In a preferred embodiment of the invention the rearward end of the stylet 124 can be curved or looped, as shown, or have a larger cross section, or can include a collar or grip to provide a better gripping surface for medical personnel. Preferably, the forward end of the endotracheal tube 102 and the stylet 124 are rounded or tapered to minimize trauma to the tissue of the patient's airway during insertion.

Figure 5:
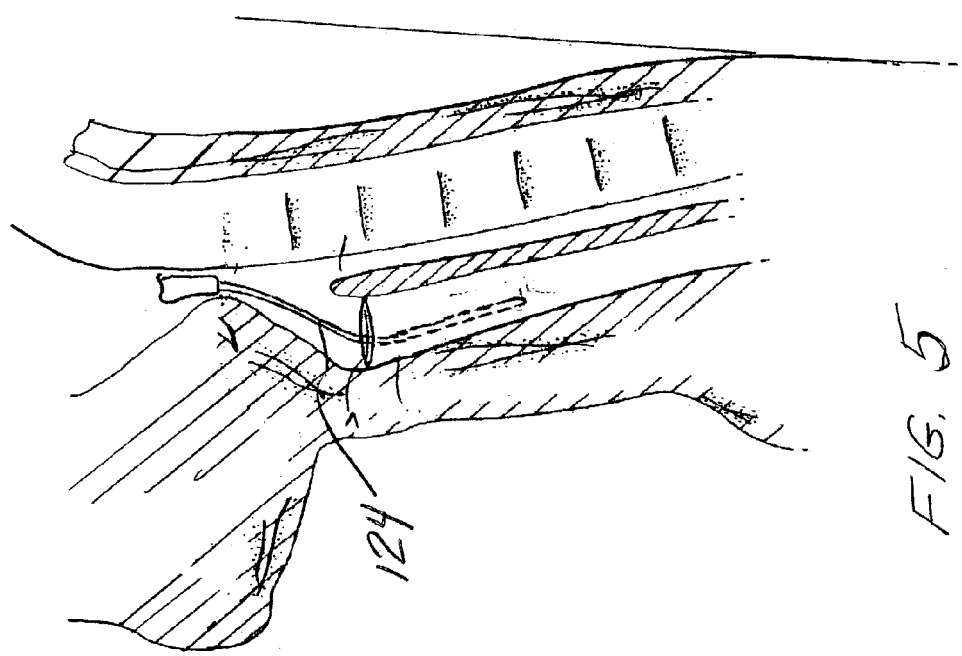
FIG. 5 is a partial view showing oral intubation of a patient utilizing the intubation device of the present invention with the stylet in its extended position within the trachea.

Referring to FIGS. 1, 5, and 6, in operation, the intubation device 100 is first bent into the desired contour (step 1) that the medical personnel believes approximates what is believed conforms to the patient's air passage way to the trachea 12. The intubation device 100 is then inserted into the patient's mouth 2 (step 2) such that the endotracheal tube 102 together with the stylet 124 are moved behind the epiglottis 4 past the esophagus 8 (FIG. 1) and towards the larynx 10. In order to aide in insertion of the endotracheal tube 102 and to avoid trauma to sensitive throat tissue, after the forward end of the intubation device 100 approaches the larynx 10, the medical personnel moves the stylet 124 forwardly such that the guide portion 128 moves longitudinally outwardly from the endotracheal tube 102 and forwardly towards and through the larynx 10 and into the trachea 12 (step 3) (FIG. 5). It should now be apparent to those skilled in the art that by reducing the risk of tissue trauma often encountered with first insertion of an endotracheal tube 102 into a patient's trachea 12, tissue swelling around the trachea 12 is minimized allowing medical personnel an unobstructed view of the larynx 10. After the guide portion 128 of the stylet 124 has been properly inserted into the trachea 12, the endotracheal tube 102 is telescopically slid or moved forwardly along the stylet 124 and guide portion 128 through the larynx 10 and into position within the trachea 12 (step 4) (FIG. 6).

Once the endotracheal tube 102 is in position within the trachea 12, air is injected through the flow valve 116, such as by a syringe, to inflate the bladder 110 (step 5). The inflated bladder 110 then operates to provide a seal to eliminate any gas that is being supplied by the endotracheal tube 102 from passing back out through the larynx 10. Medical personnel can then remove the stylet 124 (step 6) by retracting the guide portion 128 rearwardly out through the larynx 10 and out through the rearward open end 104 and fitting 118. The endotracheal tube 102 can then be connected using the adaptor 122 to a respirator or other ventilating apparatus or oxygen supply, an anesthesia supply, or some other medical gas supply. After use, the endotracheal tube 102 can be removed by first releasing air from the bladder 110 by opening the flow valve 116 and slowly withdrawing the endotracheal tube 102. The intubation device 100 is disposable and can be discarded after use.

It should be understood that the endotracheal tube 102 and stylet 124 can have a predetermined curvature to aide in the easy and quick insertion of the intubation device 100. For example, as shown in FIG. 2, the endotracheal tube 102 and stylet 124 can have a first curvature, such as shown at C1, and a second curvature, such as shown at C2. It should now be understood to those skilled in the art, however, that the endotracheal tube 102 and stylet 124 can be formed into a variety of curvatures or molded by hand to a desirable curvature. It should also now be understood to those skilled in the art that during the insertion process, if necessary, the stylet 124 can be removed and its contour adjusted and reinserted into the endotracheal tube 102 thereby adjusting its contour.

Referring now to FIGS. 3 and 7, a rearward end sectional view of the another embodiment of the intubation device 100 of the present application is shown whereby the endotracheal tube 102 includes an inner sleeve 130 (not shown in FIG. 3) that runs longitudinally along the inner wall 132 of the endotracheal tube 102 and is adapted for receiving stylet 124. In operation, the endotracheal tube 102 and stylet 124 operate as previously described, but it should now be apparent to those skilled in the art that placement of the stylet 124 within the inner sleeve 130 will permit the endotracheal tube 102 and stylet 124 to be bent into a desired contour with greater unity. In this way, the endotracheal tube 102 can be more easily bent and maintained in the desired contour. It should be understood that the inner sleeve 130 may be a singular unitary sleeve or may be formed from a plurality of cuffs and the like.

Figure 8:
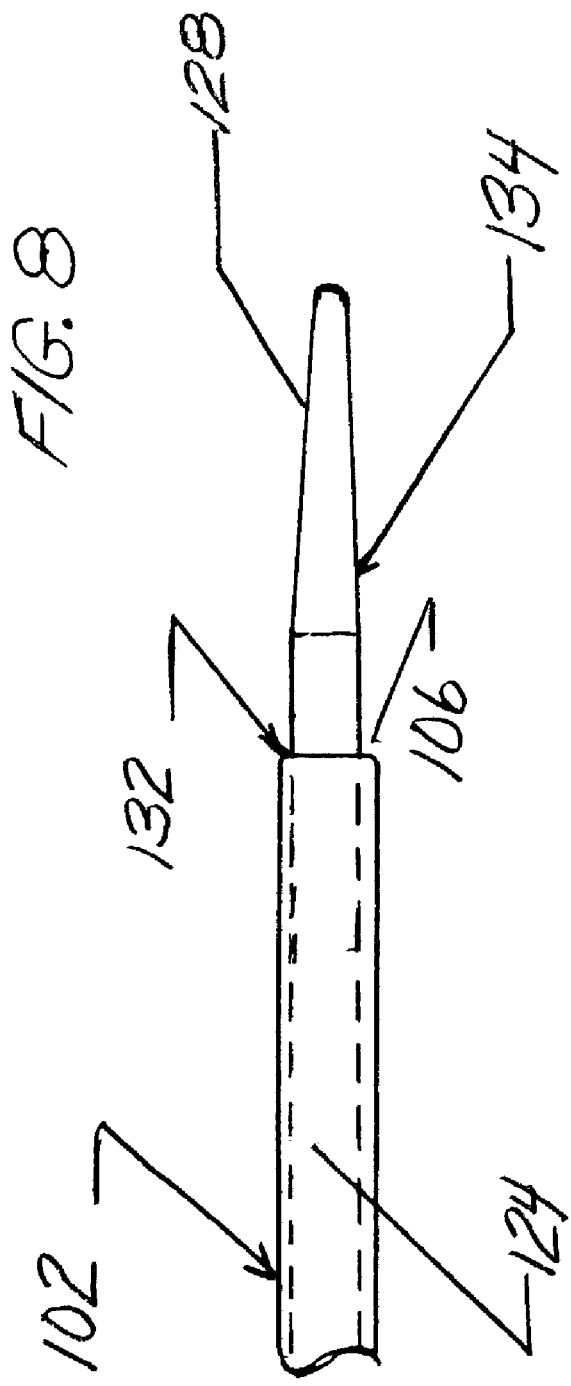
FIG. 8 is a partial view of another preferred embodiment of the invention showing the endotracheal tube and the stylet in its unsheathed position and having a taper for minimizing the lip formed between the forward open end of the endotracheal tube and the stylet.
Figure 9:
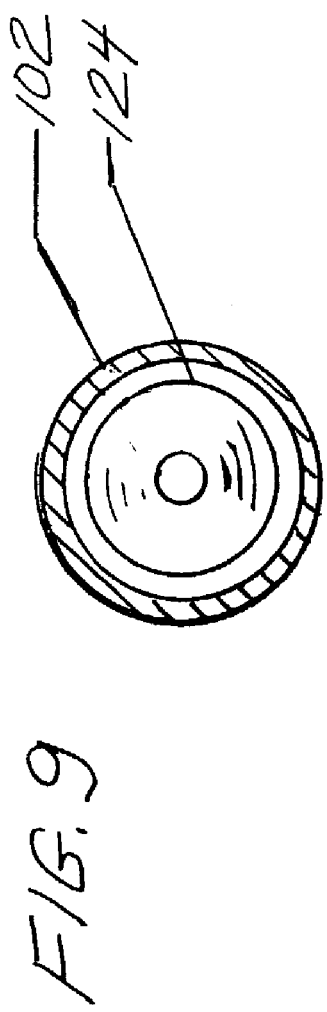
FIG. 9 is a forward end view of the stylet of FIG. 8.

Referring to FIGS. 8 and 9, as shown, the stylet 124 in shown in its unsheathed position. It should be understood to those skilled in the art that during insertion of the intubation device 100, sharp edges may result in trauma to sensitive tissue. Accordingly, it is desirable to minimize the lip 132 formed between the endotracheal tube 102 and the stylet 124 when the stylet is in its unsheatherd position. In a preferred embodiment of the invention, the diameter of the forward end of the stylet 124 decreases in a forwardly direction towards the guide portion 128 forming a taper portion 134. As shown, when the stylet 124 is extended in its unsheathed position, the taper operates to minimizing the lip 132 formed between the forward open end 106 of the endotracheal tube 102 and the stylet 124.

Referring to FIG. 10, another preferred embodiment of the invention is shown whereby the forward open end 106 of the endotracheal tube 102 includes and thin plastic or rubber membrane 136 forming a collar 138 around the stylet 124. As shown, the collar 138 operates to minimize the lip 132 formed between the endotracheal tube 102 and the stylet 124.

Referring to FIGS. 1 and 11, a rearward end view of another embodiment of the present invention is shown whereby the stylet 124 has a longitudinally extending hollow core 140 that runs the entire length of the stylet 124 having a rearward first open end 142 and a forward second open end (not shown). The first end 142 of the stylet 124 is adapted to connect to a standard oxygen supply (not shown) for ventilation. During operation, once the stylet 124 is inserted into the trachea 12, oxygen can be immediately supplied to the patient P. The endotracheal tube 102 can then be telescopically moved over the stylet 124 and into the trachea 12. The stylet 124 can then be removed. It should be apparent to those skilled in the art that the ability to inject oxygen through the stylet 124 can provide critically needed oxygen to the patient in the event insertion of the endotracheal tube 102 meets with an unexpected obstruction or resistance.

It should now be apparent to those skilled in the art that the intubation device of the present application can be easily adapted to accommodate other various mechanisms known in the art to aide in intubation of a patient. One such mechanism is shown and described in U.S. Pat. No. 5,259,377 and is incorporated herein by reference whereby the intubation device includes a mechanism comprising a flexible member positioned within the endotracheal tube that is operated by a handle means for inducing curvature to the endotracheal tube and stylet. Another such mechanism is shown and described in U.S. Pat. No. 6,539,942 and is incorporated herein by reference whereby a control wire and handgrip is provided to curve the endotracheal tube and stylet. It should be understood, however, that mechanisms for aiding in inducing curvature of the endotracheal tube and stylet are not limited to the above examples. In another preferred embodiment of the method of the present application, once the endotracheal tube 102 has been partially inserted into the air passageway of the patient P, if medical personnel find that the endotracheal tube 102 and stylet 124 do not have the proper contour, they can be adjusted into the desired contour by the adjustment mechanism. It should also be understood that the endotracheal tube 102 can remain inserted into the air passageway of the patient P and the stylet 124 removed and its contour adjusted into a desired configuration and reinserted back into the endotracheal tube 102 to adjust its contour into the desired configuration.

Referring to FIGS. 1 and 12, another preferred embodiment of the invention is shown whereby enclosed within the guide portion 128 of the stylet 124 is a vial 146 preferably formed from a pliable plastic, having a glass liner 148 containing a chemiluminescent light producing liquid reactant 150, such as bis (2, 4, 5-trichloro-6-carbopentoryphenyl) oxalate and a fluorescer in fibutyl phthalate. Positioned within the vial 146 is a sealed glass ampule 152 having an oxidizer 154, such as an 85 percent solution of hydrogen peroxide in dimethyl phthalate and a catalytic quantity of catalyst, such as sodium salicylate. In operation, prior to insertion of the intubation device 100, medical personnel activates the chemiluminescent light by bending or pressing the guide portion encompassing the vial 146 such that the glass ampule 152 breaks to allow the oxidizer 154 to mix with the reactant 150 thereby producing chemiluminescent light. In this way direct illumination of the larynx 10 and trachea 12 will be obtained.

While the intubation device and method of the present invention has been shown and described as being inserted into the patient's air pathway by way of the mouth, it should now be understood that the intubation device may also be inserted through the nose of the patient.

It should now be apparent to those skilled in the art that the intubation device of the present application can be quickly and easily inserted to form an unobstructed conduit to a patient's trachea in which oxygen, medications and therapies can be passed. It should also now be apparent to those skilled in the art that the intubation device eliminates or reduces the problems typically associated with inducers having conventional metal stylets or the like because of the soft, flexible and malleable guide portion that reduces the likelihood of trauma to the sensitive throat tissue. It should also now be apparent to those skilled in the art that the intubation device of the present invention minimizes the lip formed between the endotracheal tube and the stylet thereby reducing the likelihood of trauma to sensitive tissue. In addition, the intubation device of the present application reduces the chances of compromising the sterility of the device, and which can be relatively inexpensive to manufacture. It should also now be apparent to those skilled in the art that the intubation device is relatively easy to manipulate with one hand and allows for delicate control and sensitivity necessary to intubate a patient quickly with a minimum amount of trauma to sensitive tissue.

Although the foregoing invention has been described in some detail for purposes of clarity of understandings, it will be apparent that certain changes and modifications may be practiced within the scope of the appended claims. Furthermore, it should be noted that there are alternative ways of implementing both the method and article for implementing the method of the present invention. Accordingly, the present embodiments and examples are to be considered as illustrative and not restrictive, and the invention is not to be limited to the details given herein, but may be modified within the scope and equivalents of the appended claims.

I claim:

1. An intubation device for use in medical intubation of a patient comprising:
   an endotracheal tube having a forward open end and a rearward open end and an inner bore there between; and
   a stylet slidably positioned within said inner bore and having a rearward end, a forward end, a longitudinally extending semi-rigid portion effective for bending and maintaining the endotracheal tube in a desired contour, and a longitudinally extending elongated flexible guide portion;
   wherein, said stylet is adapted to move outwardly from said forward open end of said endotracheal tube towards the trachea such that during insertion of said endotracheal tube into the trachea of the patient said guide portion is effective for being positioned within the trachea and allowing said endotracheal tube to slide forwardly along said elongated flexible guide portion of said stylet and into proper position within the trachea; and wherein said stylet comprises a tapered portion effective for reducing the lip formed between said endotracheal tube and said stylet.

2. The intubation device of claim 1 further comprising at least one inflatable bladder for inflating and preventing ventilation gas flowing through said endotracheal tube from escaping outwardly from the trachea.

3. The intubation tube of claim 1 wherein said stylet is formed from a semi-flexible metal rod.

4. The intubation tube of claim 1 wherein said stylet is formed from copper rod.

5. The intubation device of claim 1 wherein said stylet further comprises a soft and pliable plastic sleeve.

6. The intubation device of claim 1 further comprising a light effective for illumination of the larynx and trachea of the patient.

7. An intubation device for use in medical intubation of a patient comprising:

an endotracheal tube having a forward open end and a rearward open end and an inner bore there between; and a stylet slidably positioned within said inner bore and having a rearward end, a forward end, a longitudinally extending semi-rigid portion effective for bending and maintaining the endotracheal tube in a desired contour, and a longitudinally extending elongated flexible guide portion;

wherein, said stylet is adapted to move outwardly from said forward open end of said endotracheal tube towards the trachea such that during insertion of said endotracheal tube into the trachea of the patient said guide portion is effective for being positioned within the trachea and allowing said endotracheal tube to slide forwardly along said elongated flexible guide portion of said stylet and into proper position within the trachea; and wherein said endotracheal tube comprises a collar effective for reducing the lip formed between said endotracheal tube and said stylet.

8. An intubation device for use in medical intubation of a patient comprising:

an endotracheal tube having a forward open end and a rearward open end and an inner bore there between, said endotracheal tube is formed from a pliable, semi-rigid, soft plastic material;

a stylet positioned within said inner bore and having a rearward end, a forward end, a semi-flexible portion and a longitudinally extending elongated flexible guide portion, said guide portion is formed from a soft and flexible material;

wherein said semi-flexible portion is effective for placing and maintaining said endotracheal tube in a desired contour; and wherein, said flexible guide portion is adapted to extend outwardly from said forward open end of said endotracheal tube such that during insertion of said endotracheal tube into the trachea of the patient said guide portion is positioned within the trachea and operates to guide said endotracheal tube into proper position within the trachea; and wherein the stylet comprises a tapered portion effective for reducing the lip formed between said endotracheal tube and said stylet.

9. The intubation device of claim 8 wherein said stylet further comprises a soft and pliable plastic sleeve.

10. The intubation device of claim 8 further comprising means for adjusting the contour of said endotracheal tube and said stylet while inserted into the patient.

11. The intubation device of claim 8 further comprising a chemiluminescent light effective for illumination of the larynx and trachea of the patient.

12. An intubation device for use in medical intubation of a patient comprising:

an endotracheal tube having a forward open end and a rearward open end and an inner bore there between, said endotracheal tube is formed from a pliable, semi-rigid, soft plastic material;

a stylet positioned within said inner bore and having a rearward end, a forward end, a semi-flexible portion and a longitudinally extending elongated flexible guide portion, said guide portion is formed from a soft and flexible material;

wherein said semi-flexible portion is effective for placing and maintaining said endotracheal tube in a desired contour; and wherein, said flexible guide portion is adapted to extend outwardly from said forward open end of said endotracheal tube such that during insertion of said endotracheal tube into the trachea of the patient said guide portion is positioned within the trachea and operates to guide said endotracheal tube into proper position within the trachea; and wherein said endotracheal tube comprises a collar effective for reducing the lip formed between said endotracheal tube and said stylet.

* * * * *